United States Patent
Choi et al.

(10) Patent No.: US 9,169,257 B2
(45) Date of Patent: Oct. 27, 2015

(54) CRYSTAL FORMS OF ADEFOVIR DIPIVOXIL AND PROCESSES FOR PREPARING THE SAME

(75) Inventors: Soo Jin Choi, Yongin (KR); Byung Goo Lee, Suwon (KR); Seong Soo Oh, Yongin (KR); Yong Tae Kim, Daejeon (KR); Kwang Joo Kim, Daejeon (KR); Hye Jin Kim, Daejeon (KR)

(73) Assignees: Daewoong Pharmaceutical Co., Ltd., Kyunggi-do (KR); Daewoong Bio Inc., Daejeon (KR)

( * ) Notice: Subject to any disclaimer, the term of this patent is extended or adjusted under 35 U.S.C. 154(b) by 860 days.

(21) Appl. No.: 13/256,197

(22) PCT Filed: Mar. 26, 2010

(86) PCT No.: PCT/KR2010/001867
§ 371 (c)(1),
(2), (4) Date: Nov. 29, 2011

(87) PCT Pub. No.: WO2010/110622
PCT Pub. Date: Sep. 30, 2010

(65) Prior Publication Data
US 2012/0101273 A1    Apr. 26, 2012

(30) Foreign Application Priority Data
Mar. 26, 2009 (KR) .................. 10-2009-0025879

(51) Int. Cl.
*C07D 473/34* (2006.01)
*C07F 9/6561* (2006.01)

(52) U.S. Cl.
CPC .......... *C07D 473/34* (2013.01); *C07F 9/65616* (2013.01)

(58) Field of Classification Search
CPC ..................................................... C07D 473/34
See application file for complete search history.

(56) References Cited

U.S. PATENT DOCUMENTS

| 6,451,340 B1 * | 9/2002 | Kelly et al. .................. 424/464 |
| 7,417,036 B2 | 8/2008 | Wang et al. |
| 2006/0025384 A1 | 2/2006 | Wang et al. |

FOREIGN PATENT DOCUMENTS

| CN | 1251592 A | 4/2000 |
| EP | 2411392 A2 | 2/2012 |
| JP | 2001-512712 A | 8/2011 |
| WO | 9904774 A2 | 2/1999 |
| WO | WO 99-04774 | 2/1999 |
| WO | 2010/110622 A2 | 9/2010 |

OTHER PUBLICATIONS

Extended European Search Report for EP 10756377.7 dated Nov. 9, 2012.
Japanese Office Action, dated Sep. 18, 2013, which issued during the prosecution of Japanese Patent Application No. 2012-501942.
Chinese Office Action, dated Mar. 5, 2013, which issued during the prosecution of Chinese Patent Application No. 201080013954.6.

\* cited by examiner

*Primary Examiner* — Andrew D Kosar
*Assistant Examiner* — John S Kenyon
(74) *Attorney, Agent, or Firm* — Clark G. Sullivan; Troutman Sanders LLP (57) ABSTRACT

The present invention relates to novel Forms A, B, C, D, E, F and G of crystalline 9-[2-[phosphonomethoxy]ethyl]adenine bis-pivaloyloxymethyl ester, i.e., adefovir dipivoxil, and processes for preparing them. According to the present invention, said novel crystal forms having a high purity can be obtained by a simple method and in a high yield.

5 Claims, 5 Drawing Sheets

CRYSTAL FORMS OF ADEFOVIR DIPIVOXIL AND PROCESSES FOR PREPARING THE SAME

TECHNICAL FIELD

The present invention relates to novel crystal forms of a nucleotide analog of 9-[2-[phosphonomethoxy]ethyl]adenine bis-pivaloyloxymethyl ester ("Adefovir dipivoxil") and processes for the preparation thereof.

BACKGROUND ART

Adefovir dipivoxil is an antiviral nucleotide analog, showing excellent effect as a therapeutic agent for HIV infection and hepatitis B virus (HBV) infection. The antiviral activity of said compound is shown in the references (for example, see U.S. Pat. Nos. 4,724,233 and 4,808,716; EP Patent No. 0 481 214; Benzaria et al., "Nucleosides and Nucleotide" 14(3-5): 563-565, 1995; and Starrett et al., J. Med. Chem. 37:1857-1864, 1994).

The chemical structure of adefovir dipivoxil is seen in the following formula 1:

(1)

Adefovir dipivoxil was first disclosed in EP Patent No. 0 481 214 and may exist in amorphous or crystalline forms. The amorphous form of adefovir dipivoxil can be obtained by eluting from a silica gel column using a mixture of methanol (about 4%) and methylene chloride (about 96%), and precipitating by rotary evaporation under reduced pressure at about 35° C. (see J. Med. Chem., 19:1857-1864, 1994). However, the purification and preparation of an amorphous form have the disadvantages that the procedures are not suitable for application to mass production and the amorphous form must be protected from heat, light, oxygen and moisture. Thus, as an alternative method, the crystal forms of adefovir dipivoxil were prepared and used. As an example thereof, WO04/043972 discloses a spray-drying process wherein directly prepared or commercially available adefovir dipivoxil is dissolved in an organic solvent and sprayed as micro droplets of drug solution under a high-temperature stream, and thus obtained droplets are immediately dried to give crystals. However, this method has the disadvantage of using a spray-dryer device that is not suitable for mass production. On the other hand, U.S. Pat. No. 6,451,340 discloses a method of preparing Form 2 (2 hydrate) by diluting adefovir dipivoxil solution containing 0.2% or less of water and 50% or more of 1-methylpyrrolidinone with acetone, adding n-butyl ether to produce a crystal, cooling to give Form 1, contacting said Form 1 with air having 75% or more of relative humidity or crystallizing it from a solvent containing 2-5% of water. However, this method uses a dangerous and explosive organic solvent such as n-butyl ether as the crystallizing solvent.

Polymorphism is generally considered to mean separate solids having the same molecular formula but different physical properties in melting point, solubility, density, etc. The differences in physical properties of polymorphs come from the alignments of adjacent molecules (complexes) and interactions between molecules in a bulk solid. Thus, polymorphs having the same molecular formula are unique solids in that it is not clear whether one polymorph has more advantageous physical properties than another. One of the most important physical properties of a pharmacological polymorph is water solubility, particularly solubility in the gastric juice of a patient. For example, when absorption through the intestinal tract is slow, it is desirable that the drug which is unstable under the circumstance of the stomach or intestine of a patient is slowly dissolved and not to be accumulated under this harmful circumstance. Such crystal compounds may have different fluidity, elastic deformability, dissolution rate in a pharmaceutical preparation, stability, efficacy, etc. Thus, a crystal form that is more stable, easier to handle and has a high dissolution rate is required in the art. That is, discovery of a novel crystal form of a drug would enable a skilled artisan in the field of formulation to design a pharmaceutical formulation of a drug having the desired release profile or other characteristics.

Therefore, the present inventors tried to provide a variety of novel crystal forms of adefovir dipivoxil to broaden the range of choice in preparing a pharmaceutical composition as well as to resolve the problems of the prior art in preparing the novel crystal forms.

Thus, it is one object of the present invention to provide novel crystal forms of adefovir dipivoxil.

Another object of the present invention is to provide processes for the preparation of the novel crystal forms of adefovir dipivoxil.

DISCLOSURE OF INVENTION

As a result of extensive researches for achieving the above objectives, the present inventors successfully developed novel Forms A, B, C, D, E, F and G of crystalline adefovir dipivoxil.

The novel crystal forms provided by the present invention may be more specifically defined as follows.

The XRD pattern of Form A represents the characteristic peaks at 2θ=12.9, 25.9 and 28.1. Specifically, Form A represents the powder XRD pattern of 2θ=4.4, 8.7, 12.9, 17.2, 19.8, 21.6, 25.9, 28.1 and 30.38±0.3°.

The XRD pattern of Form B represents the characteristic peaks at 2θ=7.3, 16.3, 17.2 and 22.2. Specifically, Form B represents the powder XRD pattern of 2θ=6.4, 7.3, 8.6, 9.7, 12.6, 13.5, 16.3, 17.2, 19.5, 20.8, 22.2 and 26.0±0.3°.

The XRD pattern of Form C represents the characteristic peaks at 2θ=8.1, 8.8, 9.5, 24.5, 25.3 and 32.9. Specifically, Form C represents the powder XRD pattern of 2θ=8.1, 8.8, 9.5, 15.4, 17.2, 17.6, 19.7, 21.8, 24.5, 25.3, 26.8, 28.9 and 32.9±0.3°.

The XRD pattern of Form D represents the characteristic peaks at 2θ=3.8 and 13.0. Specifically, Form D represents the powder XRD pattern of 2θ=3.8, 7.2, 10.4, 12.4, 13.0, 15.9, 17.5, 21.0 and 23.3±0.3°.

The XRD pattern of Form E represents the characteristic peaks at 2θ=3.4. Specifically, Form E represents the powder XRD pattern of 2θ=3.4, 6.9, 11.8, 12.7, 15.7, 17.2, 20.7, 21.5, 22.5 and 23.3±0.3°.

The XRD pattern of Form F represents the characteristic peaks at 2θ=5.6. Specifically, Form F represents the powder XRD pattern of 2θ=5.6, 6.9, 11.8, 12.7, 15.7, 17.2, 20.7, 21.5, 22.5 and 23.3±0.2°.

The XRD pattern of Form G has the feature of lacking the peak at 2θ=11.8, which is the characteristic peak of the Form 1 of U.S. Pat. No. 6,451,340. Specifically, Form G represents the powder XRD pattern of 2θ=6.9, 12.7, 15.7, 17.2, 20.7, 21.5, 22.5 and 23.3±0.2°.

Crystal forms are generally decided by thermodynamic characteristics such as solubility and dynamic characteristics such as several operation factors. The crystallization mechanism is decided by the operation factors, and the mechanism has influence on the formation of crystal core, growth of crystal and deformation of crystal form to give the desired crystal. Thus, analysis of the crystallization mechanism for control of the crystal form is indispensable and should be necessarily carried out in the research of crystal forms. Various methods for forming over-saturation have been studied to develop an efficient method.

It has been determined through substantial studies that the change of over-saturation according to the concentration and temperature in various solvents is the most important factor for the preparation of crystal forms of adefovir dipivoxil. The parameters having the greatest influence on the crystal form of particles when the crystal is precipitated by the core formation from the saturated solution are temperature and solvent. Various off-line methods such as X-ray diffraction analysis (XRD), differential scanning calorimetry (DSC), microscopic examination, etc. are used to examine the crystal forms obtained by the crystal-forming processes.

The starting material of adefovir dipivoxil used for preparing the novel crystal forms according to the present invention may be obtained by the art-known processes, e.g., the processes from U.S. Pat. No. 5,663,159 or J. Med. Chem., (1994) 19:1857-1864. However, the present invention sets no special limit on the process of preparing the starting material of adefovir dipivoxil.

As explained above, the present invention provides various novel crystal forms of adefovir dipivoxil and processes for preparing them. According to the present invention, the following advantages are given in this field.

First, various crystal forms provided by the present invention have the effect of broadening the spectrum of selection of the base material in preparing pharmaceutical compositions.

Second, water is used as the crystallizing solvent for preparing the crystal forms of adefovir dipivoxil in the present invention, whereby the organic solvents having some pharmaceutical restrictions remain in a less amount than in the prior arts. Furthermore, according to the present invention the production cost is reduced and its preparation including mass production becomes simple.

Third, the crystal forms of the present invention have a high recovery yield, excellent dissolution rate and storage stability.

MODE FOR THE INVENTION

In the processes for preparing the novel crystal forms according to the present invention, the kinds of novel crystals are decided by the ratio of solute (adefovir dipivoxil): good solvent: crystallization solvent, solubility condition, crystallization temperature, etc, which are explained in detail below.

1) Case of Using Water as the Crystallization Solvent

In an embodiment of the present invention, acetone is used as the good solvent in the amount of 2 to 7 times by weight, preferably 4 to 6 times by weight with respect to the weight of adefovir dipivoxil, which is the minimum amount to dissolve adefovir dipivoxil. After adefovir dipivoxil is dissolved at 10 to 40° C., preferably 20 to 30° C., water is added to the above solution as a solvent for crystallizing adefovir dipivoxil. The amount of water is 20 to 40 times by weight, preferably 25 to 30 times by weight with respect to the weight of adefovir dipivoxil. The crystallization solvent is added to form crystals and the thus-obtained mixture is stirred for 4 to 30 h, preferably 5 to 20 h while maintaining the temperature range of 0 to 30° C., preferably 5 to 25° C. to assist the formation and growth of the crystal core. The mixture is filtered, and the collected crystal is dried under reduced pressure at 35° C. or lower to give Form A of crystalline adefovir dipivoxil. After drying, Form A is determined to have a moisture content of 6.5% to 7.1% by Karl Fisher titration. If the stirring temperature is high, the yield may be reduced. Thus, the temperature and time of stirring may play an important role in obtaining the desired high yield and purity of Form A of crystalline adefovir dipivoxil.

In another embodiment of the present invention, the good solvent acetone is used in the amount of 2 to 7 times by weight, preferably 2 to 4 times by weight with respect to the weight of adefovir dipivoxil to dissolve adefovir dipivoxil at 10 to 40° C., preferably 20 to 30° C. Then, water is added to the above solution as a crystallization solvent in the amount of 7 to 13 times by weight, preferably 9 to 11 times by weight with respect to the weight of adefovir dipivoxil. The thus-obtained mixture is not stirred but is allowed to stand while being maintained at a constant cooling temperature range of 0 to 10° C., preferably 5 to 10° C. for 5 to 30 h, preferably 5 to 20 h to induce the growth of crystal. The mixture is filtered, and the collected crystal is dried under reduced pressure at 35° C. or lower. After drying, Form C is determined to have a moisture content of 6.5% to 7.1% by Karl Fisher titration.

In another embodiment of the present invention, Form A is prepared by using 1-methylpyrrolidinone or ethanol as the good solvent and water as the crystallization solvent. In the case that 1-methylpyrrolidinone is used as the good solvent to dissolve adefovir dipivoxil, it is used in the amount of 2 to 5 times by weight, preferably 3 to 4 times by weight with respect to the weight of adefovir dipivoxil. In the case that ethanol is used as the good solvent, it is used in the amount of 5 to 15 times by weight, preferably 8 to 12 times by weight with respect to the weight of adefovir dipivoxil. The thus-obtained solution is allowed to stand while maintaining the temperature at 10 to 40° C., preferably 20 to 30° C. to dissolve adefovir dipivoxil. Then, water is added to the above solution as a crystallization solvent in the amount of 10 to 30 times by weight, preferably 15 to 20 times by weight with respect to the weight of adefovir dipivoxil. In order to induce the growth of crystal, the mixture is stirred for 3 to 10 h, preferably 4 to 5 h while maintaining at a constant cooling temperature of 0 to 10° C., preferably 5 to 10° C. The mixture is filtered, and the collected crystal is dried under reduced pressure at 30° C. or lower to give Form A of crystalline adefovir dipivoxil. In the case that crystallization is performed using water as the crystallization solvent, the moisture content after drying is 6.5% to 7.1% by Karl Fisher titration.

2) The Case of Using Organic Solvents as the Good Solvent and the Crystallization Solvent The crystal forms of adefovir dipivoxil can be prepared by mixing crystallization solvents such as n-heptane or cyclohexane with the adefovir dipivoxil solution in the good solvents such as chloroform, ethyl acetate, acetonitrile or isopropyl alcohol.

In an embodiment of the present invention, adefovir dipivoxil is dissolved in the good solvent chloroform in the amount of 1 to 5 times by weight, preferably 2 to 4 times by weight with respect to the weight of adefovir dipivoxil at a temperature of 30 to 50° C., preferably 35 to 45° C. This solution is cooled to 10 to 30° C., preferably 20 to 25° C., and n-heptane is added to crystallize. The amount of n-heptane is 1 to 5 times by weight, preferably 2 to 3 times by weight with respect to the weight of adefovir dipivoxil. After crystallizing, the mixture is stirred for 4 to 20 h, preferably 5 to 10 h while maintaining the temperature of −10 to 30° C., preferably −5 to 25° C. to assist the formation and growth of the crystal core. The mixture is filtered, and the collected crystal is dried to give Form D of crystalline adefovir dipivoxil.

In another embodiment of the present invention, the good solvent ethyl acetate is used in the amount of 0.5 to 2 times by weight, preferably 0.5 to 1 times by weight with respect to the weight of adefovir dipivoxil at 10 to 40° C., preferably 20 to 30° C. to prepare a solution containing adefovir dipivoxil in high content. Then, this solution is added to n-heptane at the temperature of −20 to 20° C., preferably −5 to 5° C. to crystallize. The amount of n-heptane is 10 to 100 times by weight, preferably 20 to 50 times by weight with respect to the weight of adefovir dipivoxil. After crystallizing, the mixture is stirred for 4 to 20 h, preferably 5 to 10 h while maintaining the temperature of −20 to 20° C., preferably −5 to 5° C. to assist the formation and growth of the crystal core. The mixture is filtered, and the collected crystal is dried to give Form D of crystalline adefovir dipivoxil.

In another embodiment of the present invention, the good solvent isopropyl alcohol is used in the amount of 5 to 20 times by weight, preferably 10 to 15 times by weight with respect to the weight of adefovir dipivoxil at 10 to 40° C., preferably 20 to 30° C. to prepare a solution of adefovir dipivoxil. Then, cyclohexane is added to this solution at the temperature of 10 to 40° C., preferably 20 to 30° C. to crystallize. The amount of cyclohexane is 10 to 40 times by weight, preferably 20 to 30 times by weight with respect to the weight of adefovir dipivoxil. After crystallizing, the mixture is stirred for 10 to 40 h, preferably 15 to 25 h while maintaining the temperature of −20 to 20° C., preferably 0 to 10° C. to assist the growth of the crystal core. The mixture is filtered, and the collected crystal is dried to give Form F of crystalline adefovir dipivoxil.

In another embodiment of the present invention, the good solvent chloroform is used in the amount of 1 to 5 times by weight, preferably 2 to 3 times by weight with respect to the weight of adefovir dipivoxil at 10 to 40° C., preferably 20 to 30° C. to prepare a solution of adefovir dipivoxil. Then, n-hexane is added to this solution at the temperature of 10 to 40° C., preferably 20 to 30° C. to crystallize. The amount of n-hexane is 5 to 30 times by weight, preferably 5 to 10 times by weight with respect to the weight of adefovir dipivoxil. After crystallizing, the mixture is stirred for 1 to 10 h, preferably 2 to 5 h while maintaining the temperature of 10 to 40° C., preferably 20 to 30° C. to assist the growth of the crystal core. The mixture is filtered, and the collected crystal is dried to give Form G of crystalline adefovir dipivoxil.

3) Preparation of Form B of Crystalline Adefovir Dipivoxil

In another embodiment of the present invention, Form A of crystalline adefovir dipivoxil is prepared and filtered. The collected crystal is dried under reduced pressure at the temperature of 35 to 45° C. to give Form B of crystalline adefovir dipivoxil. The moisture content after drying is 0.01% to 0.5% by Karl Fisher titration.

4) Preparation of Form E of Crystalline Adefovir Dipivoxil

In another embodiment of the present invention, the good solvent methyl acetate or acetonitrile is used in the amount of 3 to 40 times by weight, preferably 3 to 15 times by weight with respect to the weight of adefovir dipivoxil at 10 to 40° C., preferably 20 to 30° C. to dissolve adefovir dipivoxil. The good solvent used is removed by evaporation under reduced pressure at the same temperature to give Form E of crystalline adefovir dipivoxil.

The present invention will be more specifically explained by the following examples. However, it should be understood that the examples are provided for the purpose of illustration only, and the scope of the present invention is not confined thereto.

Example 1

Preparation of Form A

Adefovir dipivoxil (0.3 g) prepared according to Example 9 of U.S. Pat. No. 5,663,159 and 1-methylpyrrolidinone (1.00 g) were mixed in the weight ratio of 1:3.33, and adefovir dipivoxil was thoroughly dissolved at 30° C. To this solution was added water controlled to 25° C. in advance until a crystal was formed. The amount of water added was 5.00 g. The solution was cooled using a refrigerator controlled to 5° C. The thus-cooled solution was stirred for about 4.5 h and the slurry was filtered to separate a crystal. The crystal obtained from filtration was washed with water and filtered again. The crystal was dried under reduced pressure at 25 to 30° C. to give 0.3 g (recovery yield: 93%) of Form A (moisture content by Karl Fisher titration: 6.7%).

Example 2

Preparation of Form A

The same procedure as Example 1 was carried out to give 0.31 g (recovery yield: 96%) of Form A (moisture content by Karl Fisher titration: 7.1%) except that adefovir dipivoxil (0.3 g) prepared according to Example 9 of U.S. Pat. No. 5,663,159 and ethanol (3.31 g) were mixed in the weight ratio of 1:11.03.

Example 3

Preparation of Form A

Adefovir dipivoxil (3.94 kg) prepared according to Example 9 of U.S. Pat. No. 5,663,159 and acetone (14.15 kg) were mixed in the weight ratio of 1:3.59, and adefovir dipivoxil was thoroughly dissolved at 30° C. To this solution was added water (141.5 kg) controlled to 25° C. in advance, and the mixture was stirred for about 10 h at 20 to 25° C. The crystal was separated by filtration and washed with water. The crystal was dried under reduced pressure at 25 to 30° C. to give 3.83 kg (recovery yield: 91%) of Form A (moisture content by Karl Fisher titration: 6.9%).

Example 4

Preparation of Form C

Adefovir dipivoxil (0.301 g) prepared according to Example 9 of U.S. Pat. No. 5,663,159 and acetone (1.30 g) were mixed in the weight ratio of 1:4.32, and adefovir dipivoxil was thoroughly dissolved at 30° C. To this solution was added water in the amount of twice the amount of acetone solvent, i.e., 2.60 g. The mixture was allowed to stand at 6.4° C. for about 17 h to induce the growth of crystal. The crystal was separated by filtration and dried under reduced pressure at 25 to 30° C. for 24 h to give 0.29 g (recovery yield: 90%) of Form C (moisture content by Karl Fisher titration: 6.5%).

Example 5

Preparation of Form D

Adefovir dipivoxil (1.00 g) prepared according to Example 9 of U.S. Pat. No. 5,663,159 and chloroform (3 g) were mixed in the weight ratio of 1:3.00, and adefovir dipivoxil was thoroughly dissolved at 45° C. The resulting solution was cooled to 25° C., and n-heptane (2.7 g) controlled to 25° C. in advance was added thereto. The mixture was cooled using a refrigerator controlled to 0° C. and stirred for about 5 h. The crystal was separated by filtration and washed with n-heptane. The crystal was dried under reduced pressure at 25 to 30° C. for 24 h to give 0.89 g (recovery yield: 89%) of Form D.

Example 6

Preparation of Form D

Adefovir dipivoxil (3.8 g) prepared according to Example 9 of U.S. Pat. No. 5,663,159 and ethyl acetate (2.7 g) were mixed in the weight ratio of 1:0.71, and adefovir dipivoxil was thoroughly dissolved at 30° C. to make a solution of high concentration. The resulting solution was added to n-heptane (82 g) maintained at 0° C., and the mixture was allowed to crystallize for about 6 h. The thus-formed crystal was separated by filtration, washed with n-heptane and filtered again. The crystal was dried under reduced pressure at 25 to 30° C. for 24 h to give 3.7 g (recovery yield: 97%) of Form D.

Example 7

Preparation of Form E

Adefovir dipivoxil (0.2 g) prepared according to Example 9 of U.S. Pat. No. 5,663,159 and methyl acetate (2.8 g) were mixed in the weight ratio of 1:14, and adefovir dipivoxil was thoroughly dissolved at 25° C. From the resulting solution, the solvent was evaporated under reduced pressure at the same temperature to give 0.18 g (recovery yield: 90%) of Form E which additionally has the peak at $2\theta=3.4°$ compared with Form 1 of U.S. Pat. No. 6,451,340.

Example 8

Preparation of Form E

The same procedure as in Example 7 was carried out except that adefovir dipivoxil (0.2 g) prepared according to Example 9 of U.S. Pat. No. 5,663,159 and acetonitrile (0.8 g) were mixed in the weight ratio of 1:4. As a result, 0.18 g (recovery yield: 90%) of Form E which additionally has the peak at $2\theta=3.4°$ compared with Form 1 of U.S. Pat. No. 6,451,340 was obtained.

Example 9

Preparation of Form F

Adefovir dipivoxil (0.5016 g) prepared according to Example 9 of U.S. Pat. No. 5,663,159 and isopropyl alcohol (6.11 g) were mixed in the weight ratio of 1:12.2, and adefovir dipivoxil was thoroughly dissolved at 30° C. To this solution was added cyclohexane in the amount of about twice the amount of isopropyl alcohol solvent, i.e., 12.83 g. Then, the mixture was stirred at 6.4° C. for about 20 h to induce the growth of crystal. The crystal was separated by filtration, washed with cyclohexane, filtered again and dried under reduced pressure at 25 to 30° C. for 24 h to give 0.45 g (recovery yield: 90%) of Form F which additionally has the peak at $2\theta=5.6°$ compared with Form 1 of U.S. Pat. No. 6,451,340.

Example 10

Preparation of Form G

Adefovir dipivoxil (0.50 g) prepared according to Example 9 of U.S. Pat. No. 5,663,159 and chloroform (1.50 g) were mixed in the weight ratio of 1:3, and adefovir dipivoxil was thoroughly dissolved at 30° C. To this solution was added n-hexane (3.03 g) controlled to the same temperature in advance. Then, the mixture was stirred for about 4 h, the crystal was separated by filtration using an aspirator and dried at 25 to 30° C. for 24 h to give 0.42 g (recovery yield: 84%) of Form G which lacks the peak at $2\theta=11.8°$ compared with the Form 1 of U.S. Pat. No. 6,451,340.

Example 11

Preparation of Form B

Form A of adefovir dipivoxil (3.83 kg), which was prepared according to the same procedure as in Example 3 and collected by filtration, was dried under reduced pressure at 35 to 45° C. to give 3.54 kg (recovery yield: 99%) of Form B of crystalline adefovir dipivoxil (moisture content by Karl Fisher titration: 0.2%).

Experiment 1

X-ray Diffraction Spectrum

Adefovir dipivoxil prepared in the examples were analyzed by X-ray diffraction analytical devices [instruments:

M18XHF-SRA (Mac Science, Japan) and Powder XRD (Bruker AXS, Germany)], and the results are represented in FIGS. 2, 3, 4, 5, 6, 7 and 8.

Experiment 2

Differential Scanning Calorimeter; DSC

Figure 1:
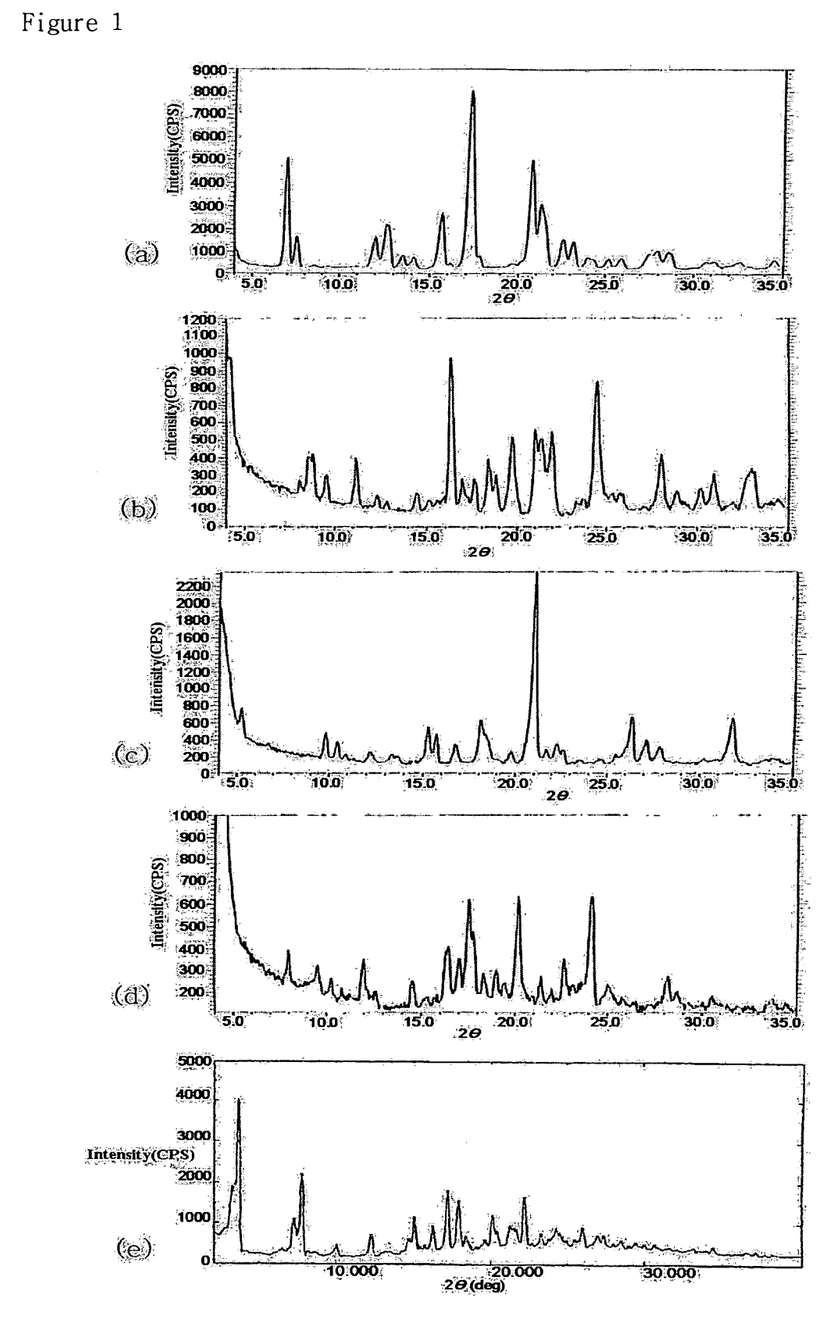
FIG. 1 represents the XRD results of known forms of crystalline adefovir dipivoxil [(a) Form 1, (b) Form 2, (c) Form 3, (d) Form 4 (Forms 1~4 are disclosed in U.S. Pat. No. 6,451,340), (e) Form of WO04/043972].
Figure 2:
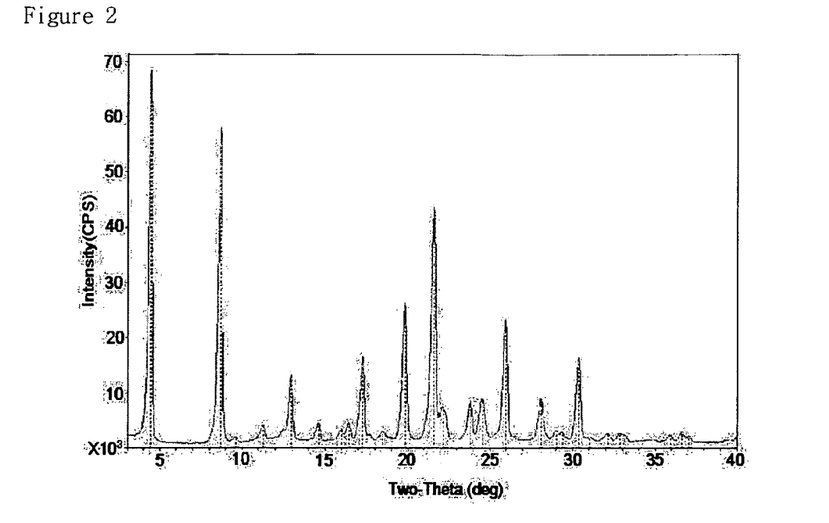
FIG. 2 represents the X-ray diffraction spectrum of Form A of crystalline adefovir dipivoxil obtained in Example 1.
Figure 3:
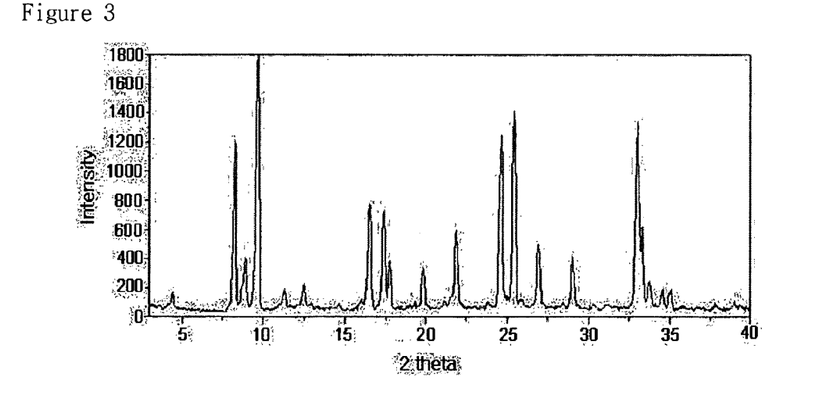
FIG. 3 represents the X-ray diffraction spectrum of Form C of crystalline adefovir dipivoxil obtained in Example 4.
Figure 4:
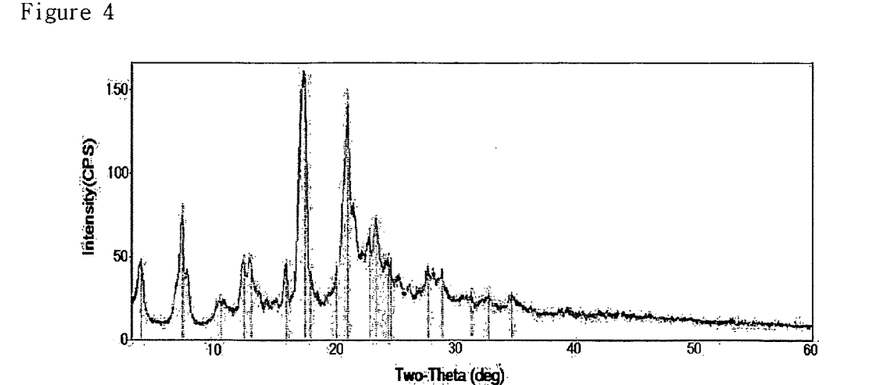
FIG. 4 represents the X-ray diffraction spectrum of Form D of crystalline adefovir dipivoxil obtained in Example 5.
Figure 5:
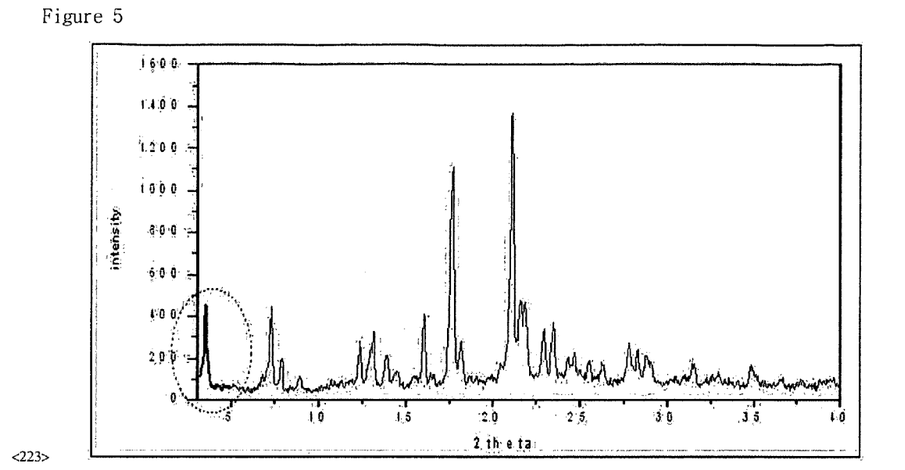
FIG. 5 represents the X-ray diffraction spectrum of Form E of crystalline adefovir dipivoxil obtained in Example 7.
Figure 6:
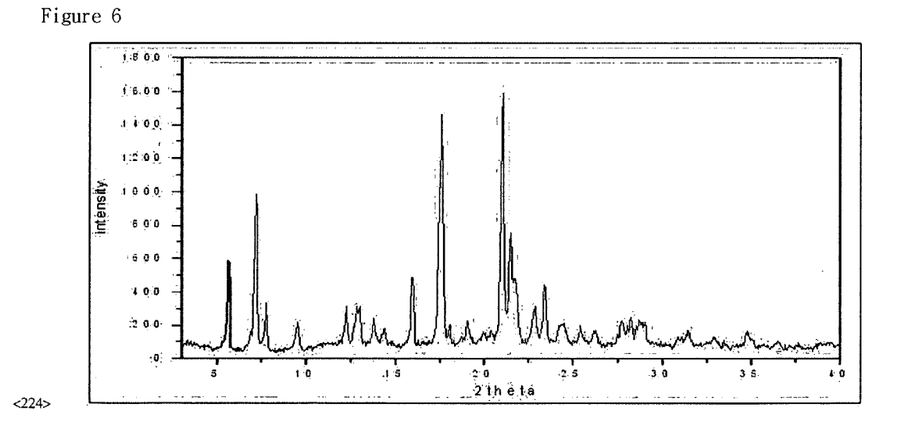
FIG. 6 represents the X-ray diffraction spectrum of Form F of crystalline adefovir dipivoxil obtained in Example 9.
Figure 7:
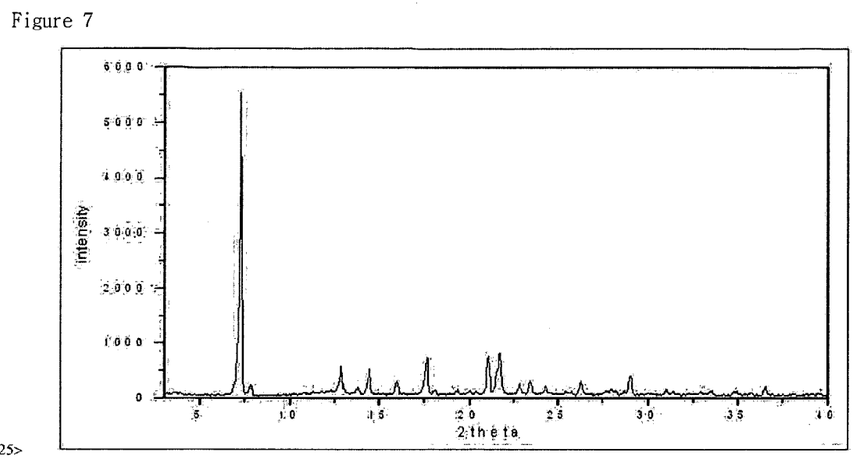
FIG. 7 represents the X-ray diffraction spectrum of Form G of crystalline adefovir dipivoxil obtained in Example 10.
Figure 8:
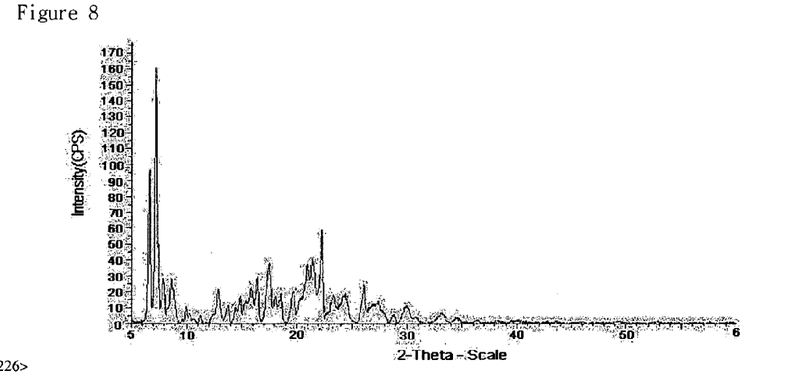
FIG. 8 represents the X-ray diffraction spectrum of Form B of crystalline adefovir dipivoxil obtained in Example 11.
Figure 9:
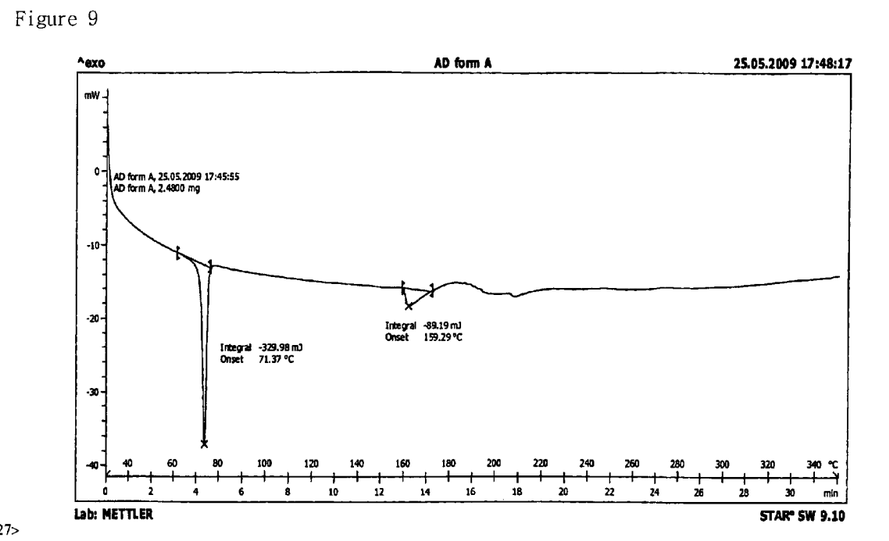
FIG. 9 represents the DSC endothermic curve of Form A of crystalline adefovir dipivoxil obtained in Example 3.
Figure 10:
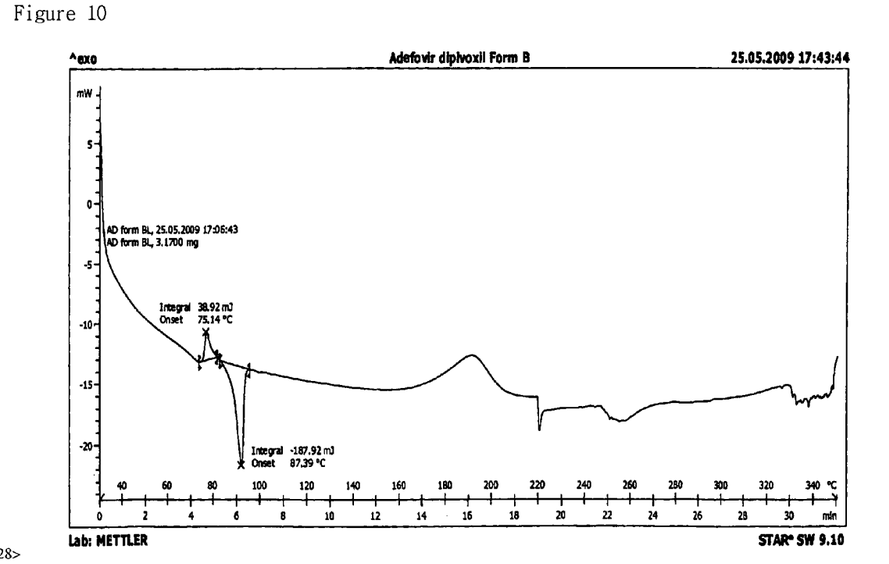
FIG. 10 represents the DSC endothermic curve of Form B of crystalline adefovir dipivoxil obtained in Example 11.

The crystal forms of adefovir dipivoxil prepared in Examples 3 and 11 were analyzed by differential scanning calorimeter [instrument: DSC822e, Mettler Toledo], and the results are represented in FIGS. 9 and 10.

Experiment 3

Drying Temperature Conditions for the Preparation of Forms a and B

Form A prepared by Example 3 was treated with various drying temperatures and drying times under the vacuum condition of 0.1~1.0 Torr, and the resulting trans-formation of the crystal form is represented in Table 1.

TABLE 1

| Material used | Drying time | Drying temperature | Crystal form |
|---|---|---|---|
| Form A prepared by Example 3 of the present invention | 10 h | 25° C. | Form A (2 hydrate) |
| | 48 h | 25° C. | Form A (2 hydrate) |
| | 10 h | 35° C. | Form B |
| | 10 h | 40° C. | Form B |
| | 10 h | 42° C. | Form B |
| | 10 h | 45° C. | Form B |
| | 10 h | 50° C. | Mixture of Form B + crystal form of Chinese Patent No. 2003100167 |
| Form I prepared by Example 1 of WO99/04774 | 10 h | 40° C. | Form I |
| | 20 h | 40° C. | Form I |

As shown in Table 1, when Form A of crystalline adefovir dipivoxil prepared according to Example 3 was vacuum dried at 25° C., it was not transformed to other crystal forms, and maintained the water content corresponding to 2 hydrate as Form A. However when dried at 35 to 45° C., it was found to be transformed from Form A to Form B. On the other hand, Form I was not transformed to Form B even when dried at the above-mentioned temperature.

Experiment 4

Stability Test

The novel Forms A and B of Examples 3 and 11 of the present invention, and 50 mg of the authentic adefovir dipivosil (purity: 99.5%) were precisely weighed into a 50 mL volumetric flask and dissolved in diluent. After making up to the mark, they were used as sample solution and standard solution, respectively. Analysis was carried out according to the following conditions, so that the contents of the novel Forms A and B, and the amounts of decomposition products of adefovir dipivoxil formed were calculated by the peak areas. The changes in the contents of novel crystal forms and the amounts of decomposition products were measured under 5° C. and accelerated condition over 6 months. The results are shown in the following Tables 2 and 3.

Analytical Conditions
Instrument: Waters HPLC model 2695
Column: Allech Mixed Mode Anion exchange C8, 7 um 100 A pore size, 250 mm×4.6 mm Analytical Conditions
Mobile phase mixing condition was operated as follows: For 19 min, mobile phase A was changed from 100% to 0%, and mobile phase B was changed from 0% to 100%. After elution with mobile phase B 100% till 36 min, the elution was changed from mobile phase A 0% to 100% till 46 min.
Mobile phase A: buffer/acetonitrile (70:30, v/v)
Mobile phase B: buffer/acetonitrile (50:50, v/v)
Buffer: 9.2 g of $K_2HPO_4$ and 47.2 g of $KH_2PO_4$ were dissolved in 2 L of purified water
Diluent: 3.4 g of $KH_2PO_4$ was dissolved in 1 L of purified water and adjusted to pH 3.0
Detector wave length: 260 nm
Flow rate: 1.2 mL/min

TABLE 2

| | | 5° C. | | | |
|---|---|---|---|---|---|
| | | Time period | | | |
| | | 0 month (%) | 1 month (%) | 3 months (%) | 6 months (%) |
| Form A | Content | 100.26 | 99.45 | 100.43 | 100.2 |
| | Total amount of decomposition product | 0.27 | 0.25 | 0.25 | 0.32 |
| Form B | Content | 100.48 | 100.34 | 99.18 | 99.74 |
| | Total amount of decomposition product | 0.38 | 0.31 | 0.36 | 0.43 |

TABLE 3

| | | Accelerated (25° C., 60% RH) | | | |
|---|---|---|---|---|---|
| | | Time period | | | |
| | | 0 month (%) | 1 month (%) | 3 months (%) | 6 months (%) |
| Form A | Content | 100.26 | 99.68 | 99.50 | 100.06 |
| | Total amount of decomposition product | 0.27 | 0.38 | 0.43 | 0.60 |
| Form B | Content | 100.48 | 98.85 | 100.25 | 99.32 |
| | Total amount of decomposition product | 0.38 | 0.42 | 0.50 | 0.66 |

As shown in Tables 2 and 3, under both 5° C. and accelerated condition, novel Forms
A and B maintained the content of 98.85%~100.48% and the total amount of decomposition product of 0.25%~0.66%, thereby exhibiting highly excellent stability.

Experiment 5

Dissolution Test

Using the novel Form B prepared in Example 11 of the present invention and the Form I prepared in Example 1 of WO99/04774 as raw materials, each formulation was manufactured by the technique disclosed in Example 1 of WO00/35460. Dissolution rates were compared in 0.01N HCl solution, pH 1.2 buffer solution (NaCl 20 g+37% HCl 68~70 mL+distilled water 9 L), pH 4.0 buffer solution (sodium acetate 7.38 g+acetic acid 25 mL+distilled water 9 L), pH 6.0 buffer solution ($KH_2PO_4$ 68 g+NaOH+distilled water 10 L) and pH 7 distilled water. Experiments were repeated 3 times for each case, and the average values are represented in Table 4.

TABLE 4

| Time (min) | | | 5 | 10 | 15 | 30 |
|---|---|---|---|---|---|---|
| Dissolution rate (%) | 0.01N HCl | Form I | 88.11 | 93.32 | 95.48 | 98.17 |
| | | Form B | 85.25 | 97.19 | 99.65 | 101.12 |
| | pH 1.2 | Form I | 95.24 | 100.90 | 101.38 | 101.61 |
| | | Form B | 93.77 | 101.06 | 102.03 | 101.71 |
| | pH 4.0 | Form I | 83.38 | 88.07 | 89.76 | 93.00 |
| | | Form B | 87.18 | 96.99 | 98.21 | 98.98 |
| | pH 6.0 | Form I | 74.89 | 89.88 | 94.58 | 97.38 |
| | | Form B | 88.62 | 95.33 | 98.01 | 100.32 |
| | Distilled water | Form I | 70.92 | 83.19 | 88.58 | 94.85 |
| | | Form B | 83.57 | 96.96 | 98.73 | 98.96 |

The results in Table 4 show that the formulation utilizing the novel Form B of the present invention exhibits a dissolution rate superior to that of the formulation utilizing the existing Form I.

The invention claimed is:

1. Crystalline adefovir dipivoxil (Form B) comprising a powder XRD pattern having characteristic peaks (2θ) at 7.3, 16.3, 17.2, and 22.2 degrees.

2. The crystalline adefovir dipivoxil of claim 1 wherein the powder XRD pattern further has characteristic peaks (2θ) at 6.4, 8.6, 9.7, 12.6, 13.5, 19.5, 20.8 and 26.0±0.3 degrees.

3. A process for preparing the crystalline adefovir dipivoxil of claim 1 comprising:
   a) dissolving adefovir dipivoxil in acetone at a weight ratio of acetone to adefovir dipivoxil of from 2:1 to 7:1, thereby forming a solution;
   b) adding water to the solution of step (a) at a weight ratio of water to adefovir dipivoxil of from 20:1 to 40:1, thereby forming adefovir dipivoxil crystals;
   c) isolating the crystals obtained in step (b); and
   d) drying said isolated crystals from step (c) at from 35° to 45° C.

4. The crystalline adefovir dipivoxil (Form B) of claim 1 in the form of an anhydrate.

5. The crystalline adefovir dipivoxil (Form B) of claim 2 in the form of an anhydrate.

* * * * *